(12) United States Patent
Wolf et al.

(10) Patent No.: US 7,553,981 B2
(45) Date of Patent: Jun. 30, 2009

(54) NATURAL SEMI-SYNTHETIC AND SYNTHETIC LIPID DERIVATIVES OF CERAMIDE AND SPHINGOSINE GROUPS, DRUGS AND THE MEDICAL USE THEREOF IN THE FORM OF THERAPEUTIC AGENTS IN PARTICULAR FOR DERMATOLOGY

(75) Inventors: Hans Uwe Wolf, Neu-Ulm (DE); Jörg Martin Dormann, Blaustein (DE)

(73) Assignee: PLT Patent and License Trading Ltd., Cambridge (GB)

( * ) Notice: Subject to any disclaimer, the term of this patent is extended or adjusted under 35 U.S.C. 154(b) by 100 days.

(21) Appl. No.: 10/559,147

(22) PCT Filed: Jun. 4, 2004

(86) PCT No.: PCT/EP2004/006076
§ 371 (c)(1),
(2), (4) Date: May 2, 2006

(87) PCT Pub. No.: WO2004/108124
PCT Pub. Date: Dec. 16, 2004

(65) Prior Publication Data
US 2006/0258616 A1    Nov. 16, 2006

(30) Foreign Application Priority Data
Jun. 6, 2003    (DE) .............................. 103 25 829

(51) Int. Cl.
  *C07F 9/02* (2006.01)

(52) U.S. Cl. .............................. 554/78; 514/53; 514/78; 536/53

(58) Field of Classification Search .................. 554/78; 514/53, 78; 536/53
See application file for complete search history.

(56) References Cited

U.S. PATENT DOCUMENTS

| 5,753,093 A | 5/1998 | Raguse et al. |
| 6,358,919 B1 | 3/2002 | Kanie et al. |
| 7,393,938 B2 * | 7/2008 | Yedgar ...................... 536/18.7 |

FOREIGN PATENT DOCUMENTS

| DE | 198 41 794 A1 | 3/2000 |
| EP | 1 201 736 A1 | 5/2002 |
| WO | WO 00/68238 A1 | 11/2000 |
| WO | WO 03/068255 A1 | 8/2003 |

OTHER PUBLICATIONS

Nicholas et al., *J. Am. Chem. Soc.*, 122, 4011-4019 (2000).
English Translation of the International Preliminary Report on Patentability for International Patent Application No. PCT/EP2004/006076.

* cited by examiner

*Primary Examiner*—Deborah D Carr
(74) *Attorney, Agent, or Firm*—Leydig, Voit & Mayer, Ltd.

(57) ABSTRACT

The subject of the present invention is new substances which are derived from naturally occurring ceramides and sphingosine and also from synthetic compounds with principally the same structure in that they represent dimers, trimers, tetramers etc., hence i.e. oligomers of the initial substances.

10 Claims, 5 Drawing Sheets

Structure and biosynthesis routes of ceramides and sphingosine

Figure 1: Structure and biosynthesis routes of ceramides and sphingosine

FIG. 2

Fig. 2: Arrangement of the lipid molecules in the typical stable structure of the lipid bilayer of biological membranes: the fatty acid radicals are orientated into the interior of the membrane and form there a hydrophobic region. The hydrophilic, polar radicals are orientated outwards in the direction of the aqueous phase, i.e. the adjacent intra- or extra-cellular fluid.

Fig. 3: Coupling of two ceramide molecules to form one dimer (a) by forming a covalent bond or (b) by inserting a short spacer (rectangle with diagonals) between the two ω-position carbon atoms respectively of a fatty acid radical of the two ceramide molecules.

Fig. 4

Fig. 4: Schematic representation of the arrangement of a "head-to-head" lipid dimer which is anchored respectively with a monomer in respectively one half of two lipid bilayers which are disposed in a parallel manner. The extended rectangle between the two monomers represents the so-called "interdimeric spacer". Only one half of the two double membranes respectively is represented.

Fig. 5: arrangement of lipid molecules comprising respectively two lipid dimers as bonding elements in a structure with two lipid bilayers.

NATURAL SEMI-SYNTHETIC AND SYNTHETIC LIPID DERIVATIVES OF CERAMIDE AND SPHINGOSINE GROUPS, DRUGS AND THE MEDICAL USE THEREOF IN THE FORM OF THERAPEUTIC AGENTS IN PARTICULAR FOR DERMATOLOGY

CROSS-REFERENCE TO RELATED PATENT APPLICATIONS

This application is the U.S. national phase of international patent application PCT/EP2004/006076, filed on Jun. 4, 2004, and claims priority to German patent application number 103 25 829.9, filed Jun. 6, 2003, all of which are hereby incorporated by reference.

The subject of the present invention is new substances which are derived from naturally occurring ceramides and sphingosine and also from synthetic compounds with principally the same structure in that they represent dimers, trimers, tetramers etc., hence therefore oligomers of the initial substances.

Basically, all biological membranes, m particular cell membranes, contain so-called lipids as essential components which structurally are constructed differently, but which resemble each other in their principal construction features. The main similarity in structure resides in the fact that they are constructed from a hydrophobic and a hydrophilic component.

Figure 1:
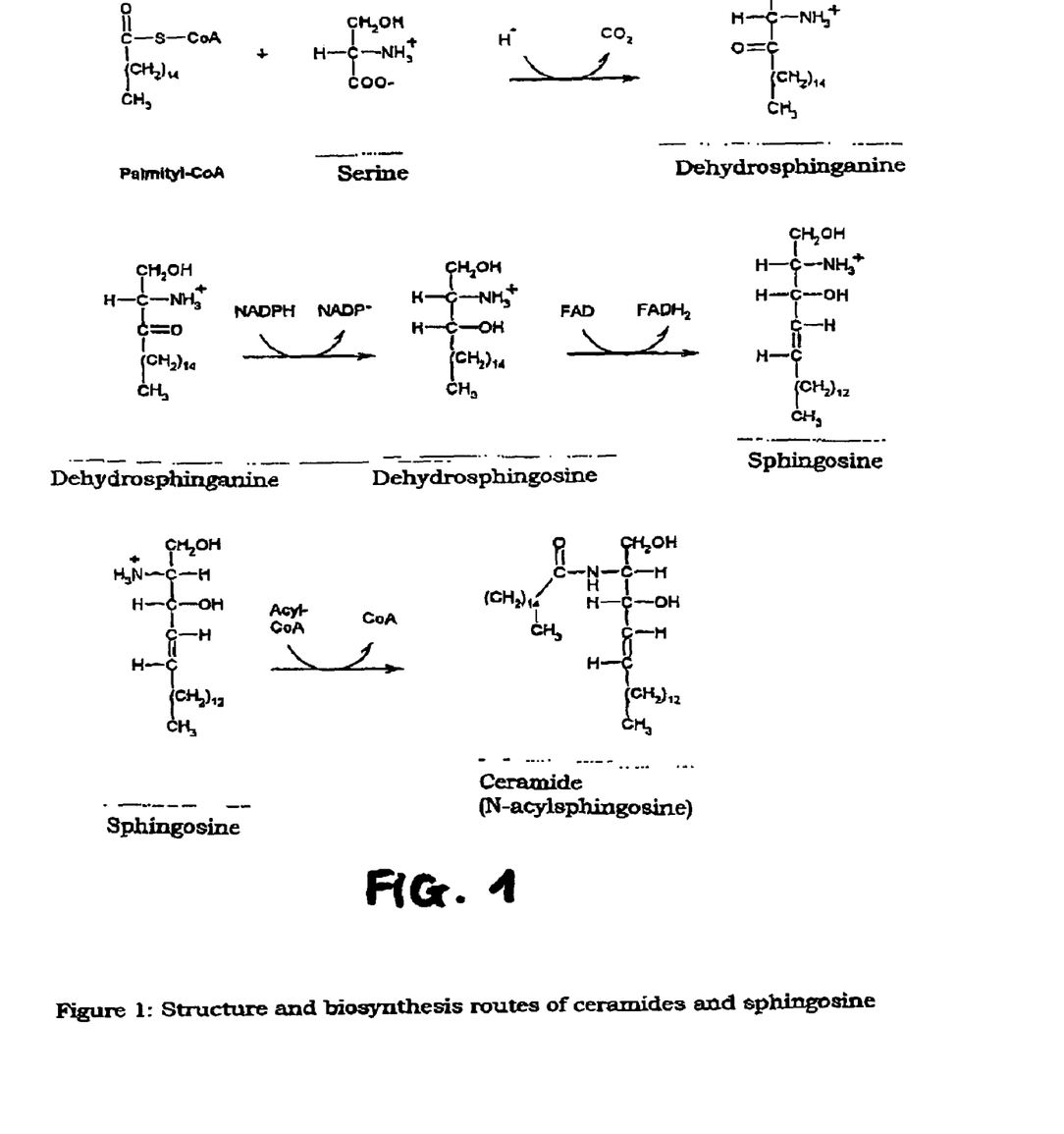
FIG. 1 shows the structure and the biosynthesis route of ceramides and sphingosine.

In the case of non-phosphatic lipids from the group of ceramides and sphingosines and also lipid-analogous substances, the hydrophobic molecule region comprises two modified fatty acid esters which are derived for example from palmitic acid, whilst the hydrophilic component is a decarboxylated serine radical. One of the two mentioned fatty acid radicals is bonded via a carboxamide bond to the nitrogen atom of the modified serine radical, whilst the second fatty acid radical is bonded on the N-bearing carbon atom of the modified serine radical. In the case of this type of cross-linkage, an α-position OH group is formed formally from the previous COOH group and a β-γ-position double bond is produced. FIG. 1 shows the structure and the biosynthesis of the lipids from the group of ceramides and sphingosines.

For the one mentioned fatty acid component of the sphingosines and for the two mentioned fatty acid components of the ceramides, there are possible, in addition to palmitic acid (n-hexadecanoic acid), $C_{15}H_{31}$—COOH, as structural elements of the mentioned lipids or lipid-analogous substances, a large number of different monocarboxylic acids, the number of chained C-atom of which is between 10 and 40. Involved herein are for example the saturated monocarboxylic acids n-dodecanoic acid (lauric acid, $C_{11}H_{23}$—COOH), n-tetradecanoic acid (myristicin acid, $C_{13}H_{27}$—COOH), n-octadecanoic acid (stearic acid, $C_{17}H_{35}$—COOH), n-icosanoic acid (arachidic acid, $C_{19}H_{39}$—COOH), n-tetracosanoic acid (lignoceric acid, $C_{23}H_{47}$—COOH), the once unsaturated cis-$\Delta^9$-hexadecenoic acid (palmitoleic acid, $C_{15}H_{29}$—COOH) and cis-$\Delta^9$-octadecenoic acid (oleinic acid, oleic acid, $C_{17}H_{33}$—COOH), twice unsaturated cis,cis-$\Delta^9$-$\Delta^{12}$-octadecadienoic acid (linoleic acid, $C_{17}H_{31}$—COOH), thrice unsaturated all-cis-$\Delta^9,\Delta^{12},\Delta^{15}$-octadecatrienoic acid (linolenic acid, $C_{17}H_{29}$—COOH) and also once hydroxylated α-hydroxytetracosanoic acid (cerebronic acid, $C_{22}H_{45}$—CHOH—COOH). Furthermore, numerous further saturated or unsaturated monocarboxylic acids which occur rarely in nature or can be produced synthetically, such as e.g. decanoic acid ($C_{10}H_{21}$—COOH), octacosanoic acid ($C_{28}H_{57}$—COOH) or cis-$\Delta^9$-octacosanoic acid ($C_{28}H_{55}$—COOH) can be used as structural components.

The amphiphilic structure of the lipids and lipid-analogous synthetic substances, i.e. the simultaneous presence of a (strongly) hydrophobic and a hydrophilic polar component of the molecule structure, leads to the fact that the lipids in an aqueous phase arrange themselves spontaneously into a lipid double layer, a so-called "lipid-bilayer", which inter alia represents the basis of the structure of biological membranes. The structural principle of this bilayer is the same for all lipids: they arrange themselves in two parallel, closely combined layers, the hydrophobic radicals of the lipid molecules being situated respectively directly opposite each other and coming into contact. They form consequently the hydrophobic inner region of the membrane bilayer, whilst the hydrophilic radicals on both sides of the lipid bilayer are in contact with the aqueous phase (see FIG. 2). The tendency towards forming this lipid bilayer exists both within and outwith an organism, e.g. in an aqueous system in which the properties of the lipid bilayers can be investigated in experimental arrangements which are designed specifically for this purpose.

Although the structure of the lipid bilayer is formed spontaneously in an organism and has considerable stability, there exists in an organism, e.g. in the presence of a lipid metabolic disturbance, the possibility that a biological membrane loses a part of its lipid components because these lipids are formed either too slowly and/or in an inadequate amount or are metabolised (too rapidly) and hence are withdrawn from the membrane structure, the relevant membranes becoming depleted of the respective lipids. This leads inter alia to a disorder of the membrane structure and function. A well known example of changes of this type is the depletion in ceramides and sphingosines of the lipid bilayers of the stratum corneum of human skin. A depletion of this type occurs demonstrably with specific skin diseases.

In particular in the field of clinical medicine, it is desirable in the mentioned cases of diseases to stabilise the structure of the biological membrane present in the organism, i.e. the lipid bilayers. This can be effected in that biological substances are used in therapeutic measures, which substances correspond to the following requirements.

the structure of the substances to be applied therapeutically should correspond to those of the membrane lipids in their fundamental constituents.

the substances to be applied therapeutically should be broken down by the metabolism processes of the organism, in particular by enzymes of the lipid metabolism, much more slowly than is the case with the original lipids.

It is the object of the present invention therefore to indicate novel lipids which are as close as possible in construction to the natural lipids, and also a pharmaceutical preparation and a corresponding application in medicine.

This object preferably is achieved by the characterizing features of the present invention. Advantageous embodiments and further developments of the solution will be apparent from the description of the invention provided herein.

The recently proposed derivatives of the lipids comprise hence oligomers of the ceramides and/or sphingosines. There should be understood by oligomers in the sense of the invention the cross-linkage of two to twelve monomers. In particular dimers, tetramers, hexamers and octamers are preferred here.

Figure 3A:
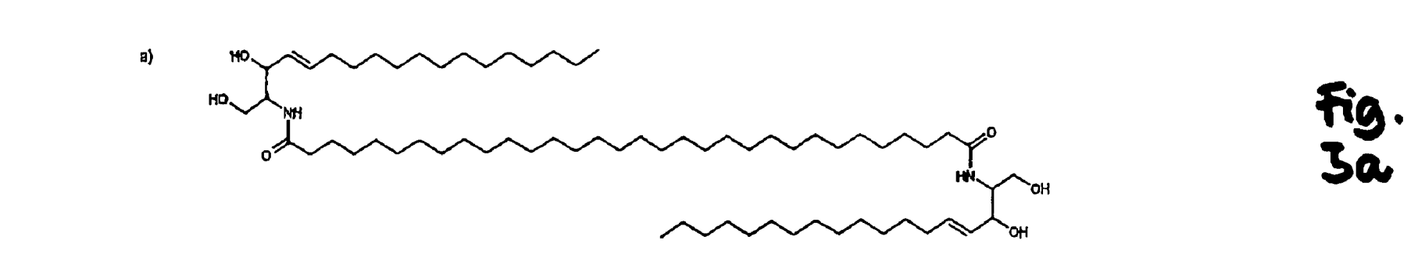
FIG. 3a shows the coupling of two ceramide molecules to form a dimer with formation of a covalent bond and FIG. 3b with a spacer.
Figure 3B:
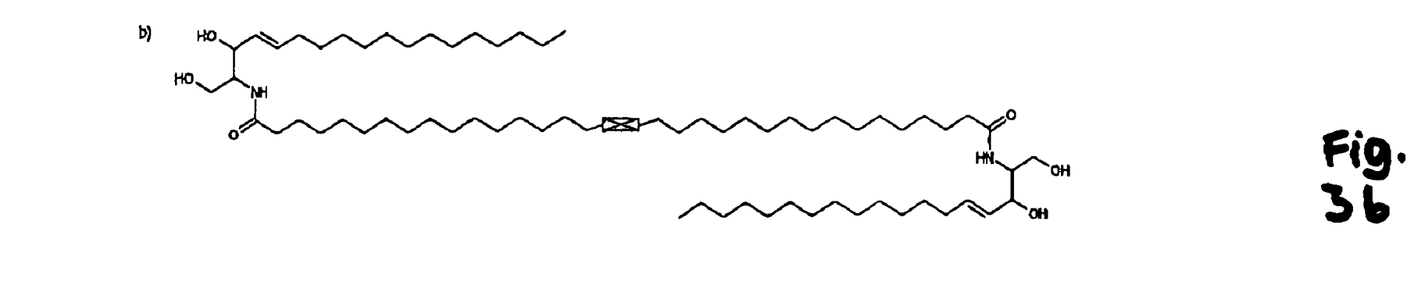

The term "dimerisation" is used in the present description and claims of the invention also when not only the direct bonding of two molecules (with doubling of the number of respectively contained atoms) is involved, but also when the two original single molecules are bonded by a short molecular bridge in the sense of a so-called "spacer" (cf. FIG. 3b).

The fatty acid components of the sphingosines and the ceramides thereby comprise preferably palmitic acid or a further arbitrary monocarboxylic acid with a chain length between 10 and 40 C-atoms.

This object preferably is achieved by the characterizing features of embodiments of the present invention.

The cross-linkage of the lipid molecules can thereby be effected in the "tail-to-tail" arrangement respectively via the hydrophobic fatty acid radical, preferably via the ω-position carbon atom of the fatty acid chain, the bonding being produced by a covalent bond. A second possibility resides in the fact that, instead of a covalent bond, a so-called "intradimeric" spacer with a freely selectable molecule chain length is used. The intradimeric spacer thereby comprises at least one carbon atom and/or at least one heteroatom, such as e.g. oxygen, nitrogen etc. Preferred chain lengths of the intradimeric spacer are 1-4 atoms.

Also in the case of cross-linkage of the lipid molecules via the "head-to-head" arrangement, this can be effected via the hydrophilic structural component by a covalent bond. In the case of the "head-to-head" cross-linkage, it is provided according to the invention as an alternative to use a so-called "interdimeric spacer" with freely selectable molecule chain length and composition. In the case where an intradimeric spacer is used, it is preferred if this is predominantly hydrophilic. Suitable structural components for a hydrophilic spacer of this type are glycerine, amino acids and/or carbohydrate components, such as monosaccharides, disaccharides, oligosaccharides etc.

The production of the lipids according to the invention is effected according to the known methods which are normal for the person skilled in the art.

The invention is explained in more detail subsequently with reference to the Figures.

Because of the structural asymmetry of the entire group of lipids—on the one side the fatty acid radical(s) as hydrophobic structural component (in English usage described as "tail") and on the other side the hydrophilic radical (in English usage described as "head")—three different ways in principle can be differentiated, as to how two monomer lipid molecules can be bonded covalently to form a dimeric lipid molecule:

1. in the form of a "tail-to-tail" arrangement, i.e. by covalent bonding between respectively one hydrophobic fatty acid radical of the two molecules to be bonded,
2. in the form of a "head-to-head" arrangement, i.e. by covalent bonding between the two hydrophilic, polar structural components of the two molecules to be bonded,
3. in the form of a "head-to-tail" arrangement, i.e. by covalent bonding between the hydrophilic polar component of the one lipid molecule and a hydrophobic fatty acid radical of the second molecule.

Variant 1, i.e. the "tail-to-tail" arrangement, is based on the cross-linkage preferably of the ω-position carbon atoms of the fatty acid radicals of both molecules to be combined. In this way, a molecule is produced which can be integrated without difficulty into a biological lipid bilayer on the basis of the arrangement of its hydrophobic molecule region. FIG. 3a shows the type of cross-linkage and the similarity of the dimerisation product to the physiological structure of the lipid double membrane in the example of two ceramide molecules (cf. FIG. 2).

Figure 2:
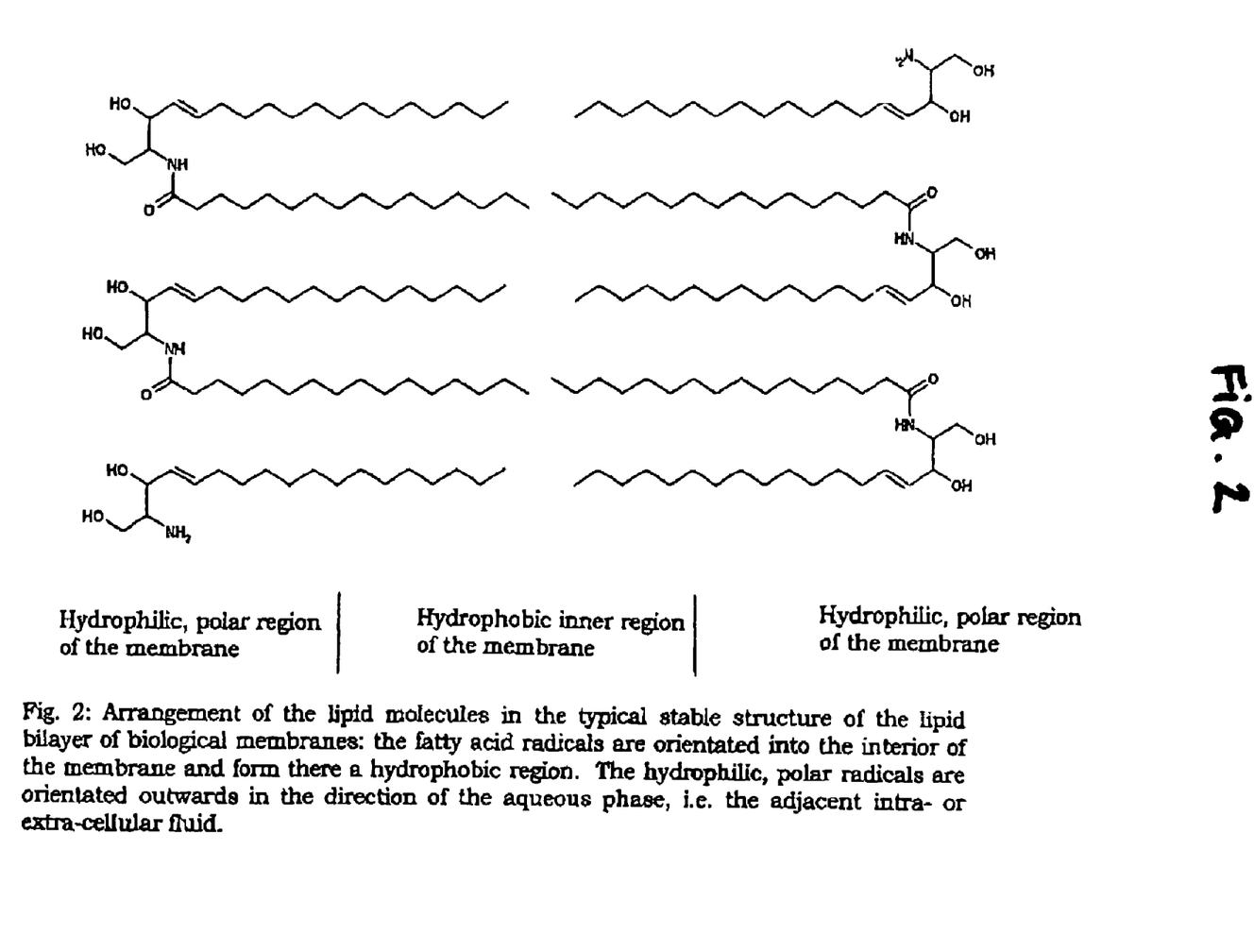
FIG. 2 shows the arrangement of the lipid molecules in a typical stable structure of the lipid bilayer of biological membranes.

The "tail-to-tail" arrangement represents direct imitation of the stable arrangement of lipid molecules which is present naturally in biological membranes, as can be detected by a comparison with the arrangement of lipids in FIG. 2. The "tail-to-tail" dimer should be regarded as the essential basic structure for the totality of all further lipid oligomers described here.

The dimerisation of the ceramide leads hence to a molecule which is inserted without problems not only in the structure of a lipid double membrane but, due to the presence of a covalent bond between the ω-positions of the fatty acid radicals of two oppositely-situated lipid molecules, contributes furthermore also to a considerable structural stabilisation of the lipid double membrane.

Variant 2, i.e. the "head-to-head" dimer, has a structure which does not allow integration of the molecule into a lipid bilayer because the hydrophilic region of this dimeric molecule would come to be situated in the hydrophobic interior of the membrane bilayer which would represent an extremely unstable structure which is consequently not formed spontaneously. The "head-to-head" dimers have however biological or medicinal importance insofar as the two lipid molecules cross-linked in this manner can be anchored in two parallel lipid bilayers which are disposed in a parallel manner at a close spacing, each of the two monomers being situated in respectively one half of the two parallel membranes.

Figure 4:
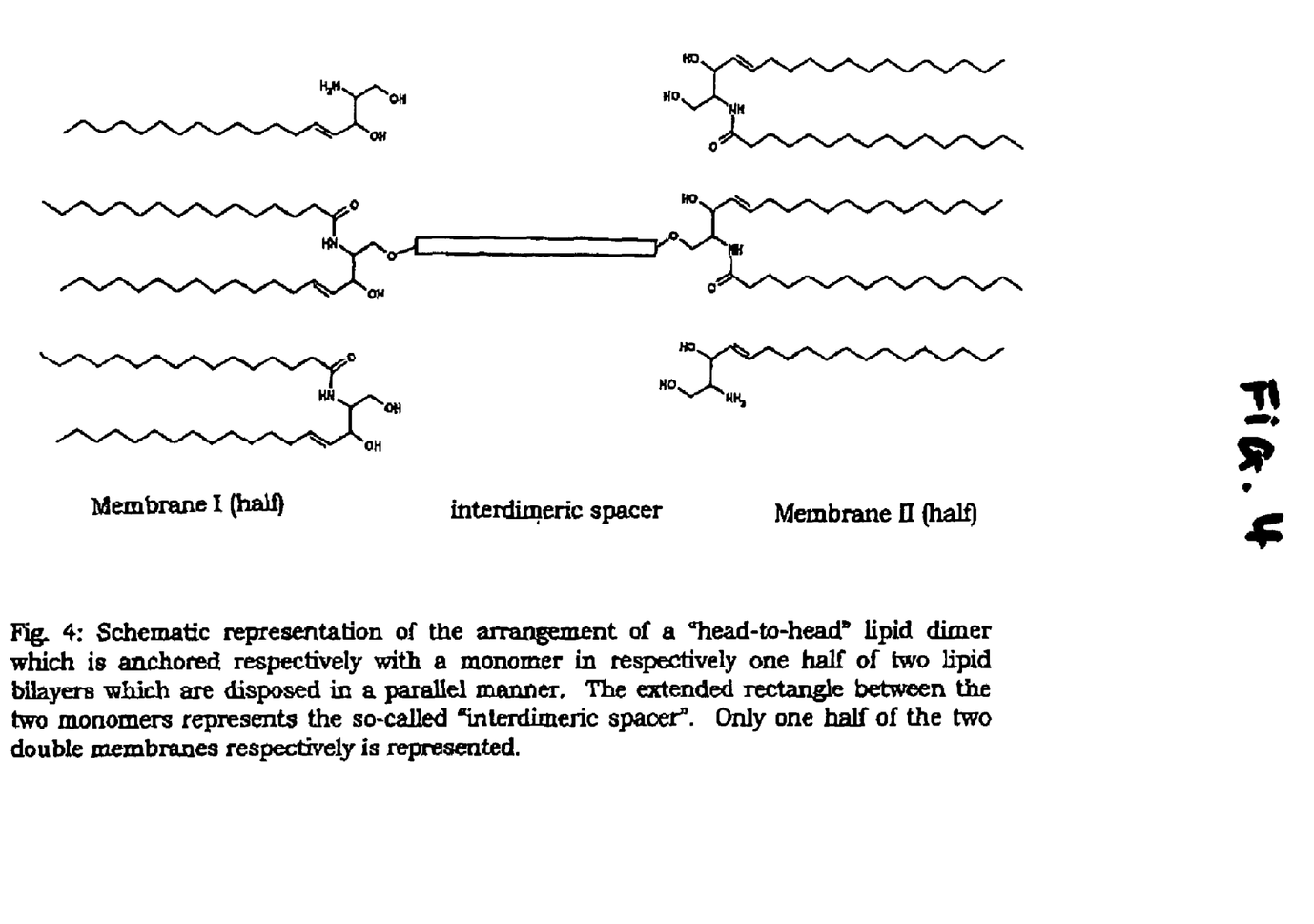
FIG. 4 shows, in schematic representation, the arrangement of a "head-to-head" lipid dimer.
Figure 5:
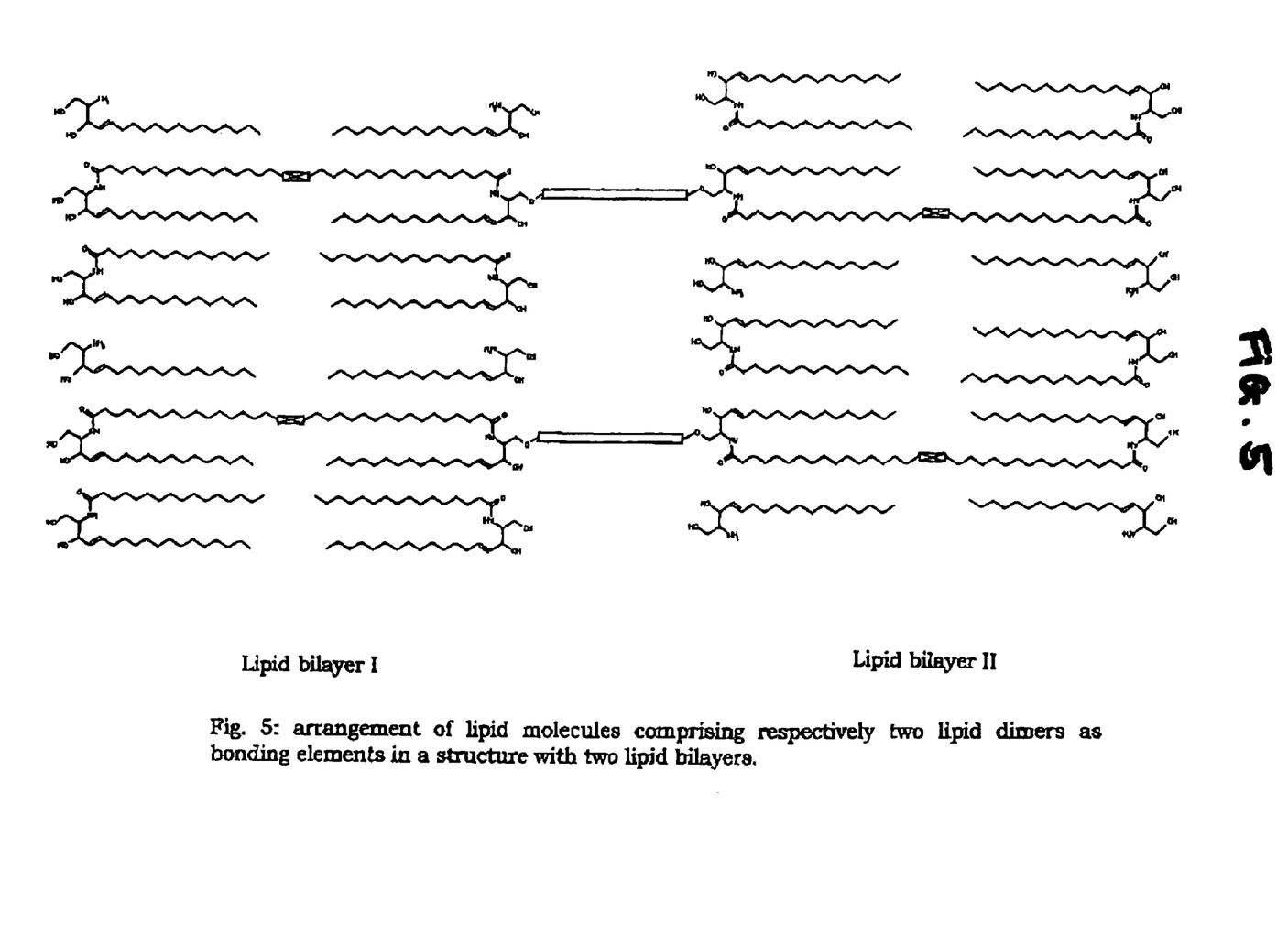
FIG. 5 shows, in schematic representation, the arrangement of lipid molecules comprising respectively two lipid dimers as bonding elements in a structure with two lipid bilayers.

In the case of the "head-to-head" lipid dimer, it can admittedly be necessary for spatial reasons to incorporate a so-called spacer (of a variable chain length) between the two monomers in order to make integration of the two lipid components in the two lipid membranes possible even when these membranes have a specific spacing from each other (see FIG. 4 in this respect). This applies for example to the lipid bilayers of the stratum corneum of human skin which are disposed in a parallel manner.

Variant 3 of the lipid dimerisation has practically no biological or medicinal importance since a molecule of this structure cannot be integrated in any manner into one or two biological membranes which are disposed in a parallel manner. In all cases, at least partly hydrophilic structural components would have to be integrated in hydrophobic regions of the membranes, which as is known would lead to very unstable structures which cannot be formed spontaneously for this reason.

The invention comprises furthermore the possibility of dimerisation in an analogous manner also for the biological precursor stages of the ceramides, i.e. for the sphingosines. Furthermore, the possibility is offered of producing hybrid molecules from respectively one molecule of ceramide and one molecule of sphingosine and of using them for therapeutic purposes in the manner described below.

Lipid oligomers of the described type can be applied everywhere in medicine for therapeutic purposes wherever the natural structure of biological membranes is disturbed by pathological processes and, by the use of these oligomeric compounds, stabilisation of the membrane structure and/or a change in membrane properties in the sense of a therapeutic goal (e.g. in order to increase the membrane fluidity) is intended to be achieved.

A few examples subsequently:

1.) In the case of specific poisonings which preferentially attack the liver, such as e.g. poisoning with tetrachloromethane (carbontetrachloride, "TETRA", $CCl_4$), the lipids of the liver cell membranes are attacked in their structure by radicals. During this process the fatty acid radicals oxidise the lipids as a result of which the carbon chain is degraded after a series of different reactions. The result thereof is partial degradation of the lipids and destabilisation of the membrane which leads to a partial dissolution of the cell membrane and hence to severe damage to the cell. The supply of the described lipid dimers can contribute in a poisoning case of this type to a significant stabilisation of the membrane of the damaged liver cells.

2.) A further example is disruption of the lipid composition of the liver cell membrane. It is known that the enzyme ceramide synthase present in the liver cell is inhibited by exogenous poisons, such as mycotoxins from the group of fumonisines. This leads to a reduction in ceramide synthesis and hence to a reduction in incorporation of ceramides in the liver cell membrane. This lack of ceramides can be compensated for by the described oligomers.

3.) A change in the lipid composition of nerve cells occurs in a large number of different pathological impairments of nerve cells. These include inter alia neuronopathy, axonopathy and myelinopathy. Exogenous pollutants are considered as causes of damage or degradation of the lipid-rich myelin sheaths. The cause of multiple sclerosis is still not yet known. In the case of myelinopathies there are considered for stabilisation of the lipid membranes of the myelin sheaths, because of their specific structure, preferably oligomers of the mentioned lipids with relatively short hydrophobic spacers between the monomers.

4.) It was able to be detected previously in several investigations that the presence of ω-3-multi-unsaturated fatty acids in lipids has an anti-thrombotic effect. The background to this effect is obviously the preferred incorporation of this lipid species in the membranes of blood cells, in particular in membranes of the blood platelets, relative to those of the lipids with ω-6-multi-unsaturated fatty acids, The use of lipid dimers with a high content of ω-3-multi-unsaturated fatty acids is possible in particular in those cases in which a genetically determined fat metabolism disorder leads to a high thrombotic, atherosclerotic and cardiovascular risk.

5.) According to current knowledge, skin diseases are one of the main fields for use of the mentioned lipid oligomers from the group of ceramides and sphingosines, not least for the reason that these two lipid species play an essential role in the stratum corneum of human skin. These possibilities for use are therefore described in detail in section 3 of the present patent specification.

A few examples are cited subsequently which describe the application of the lipids according to the invention in dermatology.

Various skin changes and skin diseases are based on changes in the lipid composition of the stratum corneum layer in human skin. These changes in the sense of a lipid loss lead to a more or less extensively reduced water-binding capacity of the affected skin parts.

Skin changes and skin diseases of this type are for example (see in this respect also Braun-Falco et al., 2002):
1. atopic dermatitis
2. "dry" skin xerosis, xerodermy
3. chronic cumulative-toxic contact eczema
4. ageing skin
5. skin greatly stressed by UV light
6. sebostasis
7. cornification disorders As already cited above, biological membranes of very many cells are constructed from a lipid bilayer which represents an effective barrier relative to the extracellular space. This also applies to the stratum corneum of the skin. In humans, this skin structure comprises a plurality of layers of keratinised corneocytes which are embedded in a lipid matrix of a highly ordered lamellar structure. These lipid bilayers contain essentially ceramides, fatty acids, such as e.g. palmitic acid and cholesterol ("cholesterin").

According to recent knowledge relating to the pathomechanism of atopic dermatitis (Arikawa, Ishibashi et al., 2002) and related diseases (Yarosh, Both and Brown, 2000), the cause of the susceptibility of the skin in the case of a disease of this type is inter alia a changed lipid metabolism or reduced lipid content of the stratum corneum. These changes relate inter alia to the ceramide and sphingosine metabolism. For example, in the case of atopic dermatitis, reduced contents inter alia of ceramide 3, ceramide 4, ω-hydroxyceramides (Macheleidt, Kaiser and Sandhoff, 2002) and sphingosine were displayed in the skin of the patients. The last of the mentioned substances has a significant antimicrobial effect. A reduced content of a substance of this type can consequently explain informally the susceptibility of atopic skin to a bacterial infection.

The physiological composition of the membrane lipids of the stratum corneum of human skin is admittedly still of essential importance for the normal structure and function of the skin for a second reason. The presence of a sufficient content of these lipids ensures the unrestricted capacity of the skin to bind a physiological quantity of water, The loss of a part of the stratum corneum lipids leads therefore to a restriction in the water-binding capacity, to the so-called transepidermal water loss of the skin. This is displayed in the occurrence of a "dry" and wrinkled skin which occurs frequently in particular, but not exclusively, in older age.

The current possibilities of relieving the symptoms and consequences of the mentioned skin diseases, in particular atopic dermatitis (at present a cure still being out of the question), are still very limited. Topical application of special glucocorticoids and immunosuppressive active substances involves considerable risks because of the toxicity of these substances. Specific corticoids even cause a precisely counterproductive effect in that they lead to a loss of ceramides, cholesterol and free fatty acids.

Taking into account the current state of knowledge relating to the importance of a physiological lipid composition of the stratum corneum membranes, it is logical that an attempt is made to compensate for the deficits in membrane lipids present in the stratum corneum by exogenous supply. In practice an attempt is therefore made, with the help of ointments, creams and the like, to supply the lacking lipids, in the present case in particular the ceramides, of changed or diseased skin. This is effected for example by lipid preparations formulated specially for this purpose with the inclusion of ceramides, inter alia by the use of liposomes. Numerous products based on existing patents are on the market in the meantime for the therapy of the mentioned skin diseases.

The therapeutic measures portrayed here should of course be regarded as correct in principle since they attempt to compensate for the present deficits in lipids of the stratum corneum in a logical manner. The knowledge gained during the last few years with these therapeutic measures shows however that, despite the correctness in principle of the therapeutic approach, the results of these curative treatments are in no way convincing. In part, the success of the implemented measures is unsure. Even when close to an apparently acceptable result of the curative treatment, a curative treatment of this type has at least two serious disadvantages:

the extent of the success of the cure is not so great that one can speak of complete recovery of the diseased skin.

in order to ensure to some extent an acceptable successful skin cure over a fairly long period of time, the mentioned lipids must be supplied permanently to the skin.

Both disadvantages can be attributed to a common cause. The mentioned lipids, such as the ceramides and sphingosines, are not static components of the skin, instead they are intermediate products of a reaction sequence in which e.g. sphingosine is converted into ceramide which for its part is converted in turn into sphingomyelin and to gangliosides. The entire reaction sequence is represented in FIG. 1.

This reaction sequence represents a flow equilibrium in which a certain quantity of the mentioned components is further processed from stage to stage by the effect of specific enzymes. Hence a certain flow rate of substance occurs. The exogenously supplied lipids, e.g. ceramides, are transferred into this reaction sequence. If a priori a disruption to this reaction sequence occurs which then leads to a pathological lipid composition of the stratum corneum then it must be expected that the exogenous supply of lipids can fundamentally change nothing or not much in this pathological state since the exogenously supplied lipid component is further processed by the organism in a similar manner, as is the case with the endogenous component of the lipids. A successful cure with the currently available therapeutic options is therefore dependent to a great extent upon the lipids in question being able to penetrate into the skin more rapidly than they are transferred into the present physiological reaction steps and upon them being supplied continuously over a fairly long period of time, in an extreme case for life.

The present problem cannot be readily solved. Certain physiological and physical-chemical or biochemical limits are set upon the rate of absorption of lipids into the stratum corneum, e.g. with respect to the diffusion rate of the lipids. This rate cannot be arbitrarily increased. On the other hand, the enzymes involved in the reaction cascade shown in FIG. 1 cannot be influenced by exogenous measures or not without serious problems.

It is necessary in order to solve this problem to apply fundamentally different principles in order to increase the therapeutic effectiveness of exogenously supplied replacement substances.

According to current knowledge, only one further possibility for intervention into the above-shown reaction sequence exists in order to ensure better and longer-lasting effectiveness of the supplied replacement lipids, i.e. the modification of the molecular structure of the lipids used for the therapy.

This modification to the molecular structure must fulfil the following three requirements.

1. The fundamental structure of the lipids used, which enables the formation of the lipid double membrane, should not only be maintained but the capacity for forming the double membrane should be increased because the skin damaged by the mentioned diseases has in any case only a restricted capacity for building up and for maintaining the physiological lipid double membrane.

2. The structure of the lipids used should be changed with the retained basic structure such that they can still function only on a smaller scale as substrates of the enzymes present in the skin, especially in the stratum corneum. This means that they should be transferred into the reaction cascade shown in FIG. 1 on a significantly smaller scale than the original lipids and hence should stay retained as essential structural components of the stratum corneum over a longer period of time than the original lipids.

3. The modification to the molecular structure should however be effected on such a small scale that, due to the small metabolically-caused modification or degradation of the supplied oligomeric supplementary lipids, such substances are produced which are as similar as possible to the body's own lipids. In this way, the danger that metabolic products with a toxic effect are produced is significantly reduced.

The mentioned modification to the molecular structure, which fulfils the three above-indicated demands, resides firstly in dimerisation of the lipids used for the expected therapeutic effectiveness. This dimerisation must be effected in the above-described variant 1, in order to imitate the arrangement of the lipids in a lipid double membrane, i.e. by cross-linkage of the hydrophobic fatty acid radicals of the mentioned lipids.

It is ensured by dimerisation of the molecule that a molecule of this type is degraded or modified very much more slowly by the enzymes of the lipid metabolism present in the skin than applies for the corresponding monomeric lipids. The enlargement of the lipid molecule associated with the dimerisation leads to a large reduction in enzymatically controlled metabolisation because, with the known high substrate specificity of most enzymes, the change in size of a substrate by the factor 2 allows the rate of the substrate conversion to drop considerably.

On the other hand, the resulting reaction products are so similar, in their general structure, to the naturally occurring analogous molecules of the lipid metabolism that transfer into the corresponding reaction sequences is possible without problems. Furthermore no heed need therefore be taken either in any way that the dimerised lipid molecules, because of the great similarity to physiologically occurring molecule species, have relevant toxicity.

The physiological degradability of the ceramide dimer and of other dimeric products, which admittedly should be significantly less than that of the simple lipid molecules, is hence a property of the molecule which is desired for pharmacokinetic and pharmacological reasons because the controllability of the therapy is consequently ensured better than if metabolic degradation were no longer possible.

In the case where the products produced from the ceramides by direct cross-linkage of the two $\omega$-position C-atoms of the fatty acid radicals have too little metabolic degradability, the following structure variant can lead as a result to an increased degradability in that quasi a "metabolic predetermined breaking point", is introduced into the molecule. In this variant, a so-called spacer, which comprises one or more C—, O— or N— atoms, is introduced between the two $\omega$-position C-atoms (FIG. 3b).

In the simplest case, this spacer can comprise an oxygen atom.

In a structural variant of this type, it would not be possible to start with the original lipid molecule in the dimerisation, but with the $\omega$-hydroxy derivatives, e.g. of the ceramide or analogous lipid molecules. The dimerisation via the ω-position carbon atom leads here not to a pure hydrocarbon chain, as shown in FIG. 3a, but to an oxygen bridging, a bridge which comprises an ether oxygen atom being produced from the two original hydroxyl groups.

The dimeric molecule produced now contains an oxygen atom at the bridging point. The carbon atoms present in the vicinity (the original ω-C-atoms) are now particularly sensitive to hydroxylation, for instance by the cytochrome-$P_{450}$-dependent mixed-functional hydroxylases. Hydroxylation of this type taking place in the direct vicinity of the O-atom leads to the formation of unstable compounds with a semi-acetal structure which break down into the corresponding reaction products. The one reaction product with a ω-position OH-group is identical to the initial product ω-hydroxyceramide. The other reaction product is a ceramide with a ω-position aldehyde function which is further oxidised to form the carboxylic acid group. It becomes hence obvious that as a result of a biochemical degradation of the described dimeric molecules (proceeding in a retarded fashion), in part the physiological initial compounds themselves and in part molecules which are very similarly constructed to the initial compounds are produced.

For reasons of an overall view, the molecule parts newly added as bridging should be described as "intradimeric spacers" henceforth. In the case discussed here the bridging oxygen atom would hence be an intradimeric spacer of this type.

In the case where the dimerisation of both lipid molecules should occur at the same time as a further controlled increase in the degradability of the resulting dimeric molecule or/and where—for instance for steric reasons—the resulting dimeric molecule should have a longer chain than corresponds to the sum of the chain lengths of the monomeric molecules, a longer intradimeric spacer can be incorporated between the two fatty acid radicals. This is achieved for example by the use of glycols, in the simplest case ethylene glycol, in order to bridge ω-hydroxyceramides. In this case, a reaction product which contains two oxygen atoms in the entire chain is produced:

The entire molecule has hence increased relative to the sum of the two monomeric molecules practically by the length of the intradimeric spacer —O—$CH_2$—$CH_2$—O—. By means of the two oxygen atoms present in this chain, the degradation rate of the lipid dimer is in general increased due to the increased oxidation capacity.

In this way, by the choice of a suitable intradimeric spacer, both the total size of the resulting dimeric molecule and also the extent of its biochemical degradability can be chosen at will because it is possible to incorporate so-called "metabolic predetermined breaking points", into the intradimeric spacer. Admittedly care must be taken that the intradimeric spacer has predominantly lipophilic properties since otherwise the possibility of integration into the lipid double membrane could be disrupted.

An essential aspect of pathogenesis of the above-mentioned skin changes or skin diseases is the reduced water-binding capacity of the skin tissue, in particular in the region of the stratum corneum. Physiologically the water is not incorporated within but, since a plurality of lipid layers disposed in parallel are present, between the individual lipid bilayers. This is due to the fact that the interior of the lipid bilayer is constructed from highly hydrophobic fatty acid esters, whilst the medium outwith the lipid bilayer is of a hydrophilic nature. Storage of water in the hydrophobic inner regions of the lipid double membrane is in practice not possible.

The above-mentioned skin changes and diseases can finally be attributed to the loss of a part of the lipid bilayers which are disposed in parallel and of the hydrophilic intermediate layers disposed between these bilayers and also water. The aim of the therapeutic measures in these diseases is hence not only the reconstruction and stabilisation of the lipid bilayers themselves, as is effected with the help of the above-described dimers of the ceramides or of the sphingosines, but furthermore also the construction and stabilisation of the multi-lamellar lipid structures with the hydrophilic intermediate layers situated therebetween which are finally of crucial importance for the water-binding capacity of the skin.

This aim is achieved in that at least two of the above-mentioned lipid dimers are cross-linked covalently. In contrast to the above-described formation of dimeric lipid molecules by creation of a covalent bond in the hydrophobic region of the molecule, i.e. at the ω-position C-atom of the fatty acid chain, the covalent bonding of two lipid dimers is effected according to a different principle.

1. The cross-linkage of two lipid dimers is effected at the hydrophilic ends of the relevant molecules, ceramide or sphingosine. As the representation of these two substances in FIGS. 1 and 2 shows, respectively one OH-group is available at the hydrophilic end of the molecule, on which the construction of larger molecules, comprising at least two lipid dimers, can be effected.

2. The cross-linkage of two lipid dimers is not effected directly, which would be possible for example with ceramides with water discharge by forming an ether-oxygen bridge. Rather it is necessary for physiological reasons to cause an intermediate space of a defined minimum size to be produced between respectively two lipid layers which are forming disposed in parallel, into which intermediate space water and if necessary hydrophilic molecules, possibly also the comparatively large molecule collagen, can be incorporated. The construction of an intermediate space is however possible when and only when the two lipid dimers to be cross-linked are retained at a spacing by a spacer which is intended to be described in the following because of its arrangement between the dimeric lipid molecules as "interdimeric spacer" (FIG. 4).

For the above-mentioned reasons—the intermediate space created by the spacer between two lipid lamellae which are disposed in parallel should be able to absorb and store water and hydrophilic molecules—the interdimeric spacer should always have hydrophilic properties. It can however be equipped with a greatly different chain length according to the above-mentioned skin disease which is present.

A few structural examples of spacer structures is intended to be given in the following, in which respectively one hydrophilic molecule structural element with a different structure and chain length is cross-linked with the OH-group which is present respectively at the hydrophilic end of the ceramide or sphingosine molecule (in these cases, in addition the —$CH_2$—O-group of both lipid components respectively is indicated):

With glycerine as spacer-forming molecule, the following structure of the intradimeric spacer with a twofold ether oxygen function is produced.

The incorporation of a dibasic amino acid such as asparaginic acid leads, with formation of two ester groupings, to a highly hydrophilic spacer:

The construction of a urea derivative as structural element of the interdimeric spacer is of particular interest. This is possible for example in combination with two molecules of an arbitrary hydrophilic amino acid, in particular a dibasic amino acid such as glutaminic acid. A particularly long spacer with a highly hydrophilic nature is hereby produced, which is provided inter alia by the presence of the two negatively charged carboxyl groups:

The construction of a urea-similar structure is of particular interest for the reason that urea has a very high water-binding capacity, which is used today already in the form of urea-containing ointments for the therapy of skin diseases in which drying-out of the skin represents a substantial feature of the illness.

Practically no limits are set upon the multiplicity of spacer structures and the length of the usable spacers. The structure just as the chain length can be varied within a wide range according to the requirement of the special therapy demands. The incorporation of specific monosaccharides, such as e.g. glucose, is also possible inter alia which in turn leads to derivatives of physiological substances. The glucosyl ceramide produced from glucose and ceramide therefore also represents a physiological substance (Ponce, Witte et al., 2001; Vielhaber, Pfeiffer et al., 2001). Further components which are suitable for chemical and biochemical reasons for constructing the interdimeric spacer are e.g. mevalonic acid and pyrrolidone carboxylic acid because (approximately) physiological compounds are hereby involved which furthermore are involved in part in the metabolism of ceramides in the sense of a synthesis stimulant (Haratake, Ikenaga et al., 2000; Aioi, Okuda et al., 2001).

The choice of the mentioned different structures in the interdimeric spacer leads to different biological stabilities and hence to a different extent of the desired degradability of the oligomeric lipid molecule which, on the one hand, should lie below the value for the monomeric lipid molecules but, on the other hand, should not be entirely lacking. Hence, via this intermolecular spacer structure, a certain controllability of the strength and duration of the effect of the lipid oligomers used for the therapy is also provided.

In the case of the metabolic degradation of the described oligomeric lipid molecules, in particular the spacers thereof, degradation products are also produced which are identical to physiological substances (e.g. amino acids+monomeric lipids) or have very great similarity to them so that the probability of undesirable side effects, i.e. toxic effects, is scarcely conceivable.

In addition to the essential effect of the ceramides, this substance group has yet a further effect. It is an activator of reactions which lead to programmed cell death (apoptosis) (Geilen, Barz and Bektas, 2001). This effect makes itself noticeable however apparently only at high intracellular ceramide concentrations. Since the active substances discussed here represent at least ceramide dimers anyway, no direct effect by them in the sense of an apoptosis can be assumed since for this they would have to be converted firstly into monomers. This degradation takes place however, as already described above, correspondingly controlled only to a slight extent.

Relative to the dimeric lipid molecules, oligomeric molecules with 2-12 monomers, in particular tetramers, hexamers or octamers, have a greater capacity to stabilise the structure of the lipid membrane bilayers which are disposed in parallel. Due to these compounds, the result is the construction of 2 parallel lamellae in the case of tetramers, 3 parallel lamellae in the case of hexamers, 4 parallel lamellae in the case of octomers etc. with an increased tendency towards incorporation of water and hydrophilic molecules of the most varied sizes into the spaces between the parallel lamellae.

Oligomeric lipids with an odd number of lipid molecules, in the simplest case thus a trimeric molecule with an intradimeric and an interdimeric spacer, can also be used perfectly well for the purposes mentioned here even if they do not have the optimal properties for integration into the lipid bilayers which are present. In the example of the trimeric lipid molecule, the two lipid molecules which are bonded via an intradimeric spacer would be integrated optimally into a lipid bilayer, whilst the further monomeric lipid molecule which is bonded via an interdimeric spacer protrudes merely into one half of the next lipid bilayer.

A lipid dimer which is bonded via an interdimeric spacer represents a special case (analogously to the above-indicated variant 2 of the cross-linkage during dimerisation). It applies also for these molecules that they can be used perfectly well for the purposes mentioned here even if they also have fewer optimal properties for integration into the lipid bilayers which are present. In this case, both lipid molecules present protrude merely into one half of the respectively adjacent lipid bilayers.

The invention claimed is:

1. Derivatives of natural, semisynthetic and synthetic lipids, the derivatives comprising oligomers of the lipids selected from ceramides and/or sphingosines, wherein, within the oligomeric lipid molecule, a cross-linkage of respectively two adjacent lipid monomers is effected strictly alternately in the "tail-to-tail" arrangement via their hydrophobic fatty acid radical directly or using an intradimeric spacer with a freely selectable molecule chain length and composition.

2. Derivatives of natural, semisynthetic and synthetic lipids according to claim 1, wherein the fatty acid component of the sphingosines and the fatty acid components of the ceramides comprise palmitic or another monocarboxylic acid with a chain length of between 10 and 40 C-atoms.

3. Derivatives of natural, semisynthetic and synthetic lipids according to claim 1, wherein the fatty acid components are selected from the group consisting of n-dodecanoic acid, n-tetradecanoic acid, n-octadecanoic acid, n-icosanoic acid, n-tetracosanoic acid, cis-$\Delta^9$-hexadecenoic acid, cis-$\Delta^9$-octadecenoic acid, cis,cis-$\Delta^{9-\Delta 12}$-octadecadienoic acid, all-cis-$\Delta^9$,$\Delta$-$^{12}$,$\Delta^{15}$-octadecatrinoic acid, α-hydroxytetracosanoic acid, decanoic acid, octacosanoic acid, and cis-$\Delta^9$-octacosanoic acid.

4. Derivatives of natural, semisynthetic and synthetic lipids according to claim 1, wherein, the intradimeric spacer comprises at least one carbon atom and/or at least one heteroatom.

5. Derivatives of natural, semisynthetic and synthetic lipids according to claim 1, wherein two adjacent lipid molecules are bonded to each other in the "head-to-head" arrangement respectively via their hydrophobic structural component.

6. Derivatives of natural, semisynthetic and synthetic lipids according to claim 1, wherein two adjacent lipid molecules are bonded in the "head-to-head" arrangement via an intradimeric spacer with a freely selectable molecule chain length and composition.

7. Derivatives of natural, semisynthetic and synthetic lipids according to claim 1, wherein the intradimeric spacer is predominantly hydrophilic.

8. Derivatives of natural, semisynthetic and synthetic lipids according to claim 6, wherein the interdimeric spacer contains structural components selected from the group consisting of glycerine, amino acids, carbohydrate components, mevalonic acid, and pyrrolidone carboxylic acid.

9. Derivatives of natural, semisynthetic and synthetic lipids according to claim 1, wherein two adjacent lipid molecules are bonded respectively in the "tail-to-tail" arrangement via the ω-position carbon atom of the fatty acid chain, by a covalent bond.

10. Pharmaceutical preparation containing lipids according to claim 1 as active substance.

* * * * *